US005919229A

United States Patent [19]
Portney

[11] Patent Number: 5,919,229
[45] Date of Patent: *Jul. 6, 1999

[54] MULTIFOCAL OPTHALMIC LENS

[75] Inventor: Valdemar Portney, Irvine, Calif.

[73] Assignee: Allergan, Waco, Tex.

[*] Notice: This patent is subject to a terminal disclaimer.

[21] Appl. No.: 08/885,987

[22] Filed: Jun. 30, 1997

Related U.S. Application Data

[62] Division of application No. 08/592,752, Jan. 26, 1996, Pat. No. 5,702,440.

[51] Int. Cl.$^6$ .................................. A61F 2/16; A61F 2/14
[52] U.S. Cl. ..................................... 623/5; 623/6; 351/161
[58] Field of Search ........................ 623/4–6; 351/160 R, 351/161

[56] References Cited

U.S. PATENT DOCUMENTS

| Re. 25,286 | 11/1962 | DeCarle . |
| 1,483,509 | 2/1924 | Bugbee . |
| 2,129,305 | 9/1938 | Feinbloom . |
| 2,274,142 | 2/1942 | Houchin . |
| 2,405,989 | 8/1946 | Beach . |
| 2,511,517 | 6/1950 | Spiegel . |
| 3,004,470 | 10/1961 | Ruhle . |
| 3,031,927 | 5/1962 | Wesley . |
| 3,034,403 | 5/1962 | Neefe . |
| 3,210,894 | 10/1965 | Bentley . |
| 3,227,507 | 1/1966 | Feinbloom . |
| 3,339,997 | 9/1967 | Wesley . |
| 3,420,006 | 1/1969 | Barnett . |
| 3,431,327 | 3/1969 | Tsuetaki . |
| 3,482,906 | 12/1969 | Volk . |
| 3,542,461 | 11/1970 | Girard et al. . |
| 3,693,301 | 9/1972 | Lemaltre . |
| 3,794,414 | 2/1974 | Wesley . |
| 3,932,148 | 1/1976 | Krewalk, Sr. . |
| 4,055,378 | 10/1977 | Feneberg et al. . |
| 4,062,629 | 12/1977 | Winthrop .................................. 351/169 |

(List continued on next page.)

FOREIGN PATENT DOCUMENTS

| 3225789 | 10/1989 | Australia . |
| 59395 | 12/1914 | Canada . |
| 0140603 | 5/1985 | European Pat. Off. . |
| 0351471 | 1/1990 | European Pat. Off. . |
| 2702117 | 7/1978 | Germany . |

(List continued on next page.)

OTHER PUBLICATIONS

"Lens Design Fundamentals"; R. Kingslake; Institute of Optics University of Rochester, Rochester, NY; Academic Press 1978; pp. 36–39.

Jan. 1988, Article: Contact Lens Practice.

Sep. 1960, Article: Encyclopedia of Contact Lens Practice.

Jun. 1960, Article: Further Developments of Bifocal Contact Lenses pp. 185–186, Contacto, The Contact Lens Journal (1959).

"The Shah Bifocal Intraocular Lens Implant", Shah & Shah Intraocular Lens Laboratories, Calcutta, India.

"A Three–Part System for Refining Intraocular Lens Power Calculations", *Journal of Cataract and Refractive Surgery*, J.T. Holladay, M.D., et al., vol. 14, Jan. 1988, pp. 17–23.

*Primary Examiner*—David H. Willse
*Attorney, Agent, or Firm*—Frank J. Uxa

[57] ABSTRACT

A multifocal ophthalmic lens, having outer annular zones with vision correction powers less than a far vision correction power of the patient, is disclosed. These additional annular zones come into play, when the pupil size increases under dim lighting conditions, to thereby compensate for the near-vision powered annular zones. The net effect of the additional near vision annular zones and the additional annular zones having power less than the far vision correction power is to shift the best quality image from in front of the retina to an area on the retina of the eye, to thereby reduce halo effects and improve image contrast.

7 Claims, 2 Drawing Sheets

U.S. PATENT DOCUMENTS

| | | | |
|---|---|---|---|
| 4,073,579 | 2/1978 | Deeg et al. . | |
| 4,195,919 | 4/1980 | Shelton . | |
| 4,199,231 | 4/1980 | Evans | 351/160 H |
| 4,210,391 | 7/1980 | Cohen | 351/161 |
| 4,240,719 | 12/1980 | Guilino et al. | 351/169 |
| 4,274,717 | 6/1981 | Davenport | 351/169 |
| 4,307,945 | 12/1981 | Kitchen et al. | 351/169 |
| 4,315,673 | 2/1982 | Guilino et al. | 351/169 |
| 4,338,005 | 7/1982 | Cohen | 351/161 |
| 4,340,283 | 7/1982 | Cohen | 351/161 |
| 4,377,329 | 3/1983 | Polar | 351/160 R |
| 4,402,579 | 9/1983 | Polar | 351/160 R |
| 4,418,991 | 12/1983 | Breger | 351/161 |
| 4,504,982 | 3/1985 | Burk | 623/6 |
| 4,573,775 | 3/1986 | Bayshore | 351/161 |
| 4,580,882 | 4/1986 | Nuchman et al. | 351/161 |
| 4,596,578 | 6/1986 | Kelman | 623/6 |
| 4,618,228 | 10/1986 | Baron et al. | 351/161 |
| 4,618,229 | 10/1986 | Jacobstein et al. | 351/161 |
| 4,636,049 | 1/1987 | Blaker | 351/161 |
| 4,636,211 | 1/1987 | Nielsen et al. | 623/6 |
| 4,637,697 | 1/1987 | Freeman | 351/161 |
| 4,641,934 | 2/1987 | Freeman . | |
| 4,693,572 | 9/1987 | Tsuetaki et al. | 351/161 |
| 4,704,016 | 11/1987 | de Carle | 351/161 |
| 4,720,286 | 1/1988 | Bailey et al. | 623/6 |
| 4,752,123 | 6/1988 | Blaker | 351/161 |
| 4,759,762 | 7/1988 | Grendahl | 623/6 |
| 4,769,033 | 9/1988 | Nordan | 623/6 |
| 4,813,955 | 3/1989 | Achatz et al. | 623/6 |
| 4,830,481 | 5/1989 | Futhey et al. | 351/161 |
| 4,881,804 | 11/1989 | Cohen | 351/161 |
| 4,890,912 | 1/1990 | Visser | 351/161 |
| 4,890,913 | 1/1990 | DeCarle | 351/161 |
| 4,898,461 | 2/1990 | Portney | 351/169 |
| 4,906,246 | 3/1990 | Grendahl | 623/6 |
| 4,917,681 | 4/1990 | Nordan | 623/6 |
| 4,919,663 | 4/1990 | Grendahl | 623/6 |
| 4,921,496 | 5/1990 | Grendahl | 623/6 |
| 4,923,296 | 5/1990 | Erickson | 351/161 |
| 4,938,583 | 7/1990 | Miller | 351/161 |
| 4,976,534 | 12/1990 | Miege | 623/6 X |
| 5,000,559 | 3/1991 | Takahashi et al. | 351/169 |
| 5,002,382 | 3/1991 | Seidner | 351/161 |
| 5,019,099 | 5/1991 | Nordan | 623/6 |
| 5,089,024 | 2/1992 | Christie et al. | 623/6 |
| 5,096,285 | 3/1992 | Silberman | 623/6 X |
| 5,112,351 | 5/1992 | Christie et al. | 623/6 |
| 5,166,711 | 11/1992 | Portney | 623/6 X |
| 5,192,317 | 3/1993 | Kalb | 623/6 |
| 5,225,858 | 7/1993 | Portney | 623/6 X |
| 5,270,744 | 12/1993 | Portney | 623/6 X |
| 5,682,223 | 10/1997 | Menezes et al. | 623/6 |

FOREIGN PATENT DOCUMENTS

| | | |
|---|---|---|
| 888414 | 11/1988 | South Africa . |
| 939015 | 10/1963 | United Kingdom . |
| 2058391 | 4/1981 | United Kingdom . |
| 2129155 | 5/1984 | United Kingdom . |
| 2146791 | 4/1985 | United Kingdom . |
| 2192291 | 1/1988 | United Kingdom . |
| WO87/00299 | 1/1987 | WIPO . |
| WO86/03961 | 12/1987 | WIPO . |
| WO87/07496 | 12/1987 | WIPO . |
| 8902251 | 3/1989 | WIPO . |
| 8911672 | 11/1989 | WIPO . |
| 9000889 | 2/1990 | WIPO . |

MULTIFOCAL OPTHALMIC LENS

This is a division of application Ser. No. 08/592,752 filed Jan. 26, 1996, now U.S. Pat. No. 5,702,440.

FIELD OF THE INVENTION

The present invention relates generally to ophthalmic lenses and, more particularly, to a multifocal ophthalmic lens adapted for implantation in an eye, such as an intraocular lens, or to be disposed in a cornea, such as a corneal inlay.

BACKGROUND OF THE INVENTION

The general construction of a multifocal ophthalmic lens is known in the art. U.S. Pat. No. 5,225,858, which is incorporated herein by reference, discloses a multifocal ophthalmic lens including a central zone circumscribed by multiple concentric, annular zones. This patent discloses a means of providing improved image quality and light intensity for near images. The improved image quality is accomplished by maintaining the near vision correction power of appropriate zones of the lens substantially constant for a major segment of the near vision correction power region of each zone, and by providing a central zone having an increased depth of focus.

The major segment of each near vision correction power region, which has a substantially constant near vision correction power, inherently reduces the depth of focus associated with far vision. The location of near focus is typically immaterial for near vision, because of the ability of the user to easily adjust the working distance of the target object. The patent discloses progressive vision correction powers in the central zone for extending the depth of focus. The increased depth of focus provided by the central zone helps to compensate for the reduction in depth of focus associated with the near vision correction power regions. This feature is particularly applicable to an intraocular lens, since the patient has minimal residual accommodation, i.e., the ability of a normal eye to see objects at different distances.

FIG. 1 shows how the multifocal ophthalmic lens 6 of the prior art focuses parallel incoming light onto the retina 10 of the eye. For the normal lighting condition with a 3 mm pupil diameter, the rays 7 pass through a far focus region of the multifocal ophthalmic lens 6, and are focused onto the retina 10. The rays 8 pass through a near region of the multifocal ophthalmic lens 6, and are focused into a region between the retina 10 and the multifocal ophthalmic lens 6.

The multifocal ophthalmic lens 6 shown in FIG. 1 shows the passage of parallel rays through the multifocal ophthalmic lens 6 in a well-lit environment. In low lighting conditions, the pupil enlarges, and additional annular zones of the multifocal ophthalmic lens 6 become operative to pass light therethrough. These additional annular regions operate to provide additional far (rays 9 in FIG. 1) and near-focus corrective powers to the multifocal ophthalmic lens 6. Presence of the additional intermediate and near rays shift the best image quality for far vision to the location in front of the retina. As a result, in low lighting conditions the best quality image of the multifocal ophthalmic lens 6 appears in a region slightly in front of the retina 7. A user looking through the multifocal ophthalmic lens 6 while driving at night, for example, may notice an undesirable halo affect around a bright source of light. The shift in the best quality image just in front of the retina 7 instead of on the retina 7 increases the halo effect making driving for some people difficult.

A problem has thus existed in the prior art of providing a multifocal ophthalmic lens, which can provide a desirable far vision correction in low lighting conditions, but which does not unnecessarily elevate halos and contrast reductions under increased pupil size which usually occurs in low lighting conditions. Thus, the prior art has been unable to produce a multifocal ophthalmic lens, which achieves a best quality image on the retina (instead of slightly in front of the retina) in low lighting conditions.

Under low lighting conditions, the best quality image of prior art multifocal ophthalmic lenses is not focused on the retina of the eye. Instead, these prior art multifocal ophthalmic lenses have a best quality image in front of the retina in low lighting conditions, which corresponds to a mean power of the multifocal ophthalmic lens being slightly higher than the far vision correction power required for the patient.

SUMMARY OF THE INVENTION

As light diminishes and pupil size correspondingly increases, the outer annular zones of a multifocal ophthalmic lens begin to pass light therethrough. These outer annular zones traditionally introduce additional near vision correction power, which effectively shifts the best quality image from on the retina to an area slightly in front of the retina.

The outer annular zones of the present invention have vision correction powers, which are less than the far vision correction power of the patient, to compensate for the increase in the mean power of the multifocal ophthalmic lens. A multifocal ophthalmic lens, having outer annular zones with vision correction powers less than a far vision power of the patient, is disclosed. The additional annular zone or zones come into play when the pupil size increases under dim lighting conditions, to thereby compensate for the additional near vision annular zones introduced by the enlarged pupil size. The net effect of the additional near vision annular zones and the additional annular zones having power less than the far vision correction power is to focus the best quality image onto the retina of the eye, to thereby reduce halo effects and improve contrast.

The multifocal ophthalmic lens of the present invention is adapted to be implanted into an eye or to be disposed in a cornea, and has a baseline diopter power for far vision correction of the patient. The multifocal ophthalmic lens includes a central zone having a mean vision correction power equivalent to or slightly greater than the baseline diopter power depending upon pupil size, and includes a first outer zone located radially outwardly of the central zone.

A second outer zone located radially outwardly of the first outer zone provides vision correction power, that is less than the baseline diopter power. The vision correction power of the second outer zone can be substantially constant. Light generally does not pass through the second outer zone under bright lighting conditions.

A third outer zone of the multifocal ophthalmic lens comes into play in lower lighting conditions, and includes a vision correction power greater than the baseline diopter power. A fourth outer zone circumscribes the third outer zone, and includes a vision correction power, that is less than the baseline diopter power. This fourth outer zone passes light in very low lighting conditions, when the pupil is significantly dilated. The second and fourth outer zones serve to focus light slightly behind the retina of the eye, to thereby compensate for light focused in front of the retina of the eye by the first and third outer zones, under dim lighting conditions.

BRIEF DESCRIPTION OF THE PREFERRED EMBODIMENTS

Figure 1:
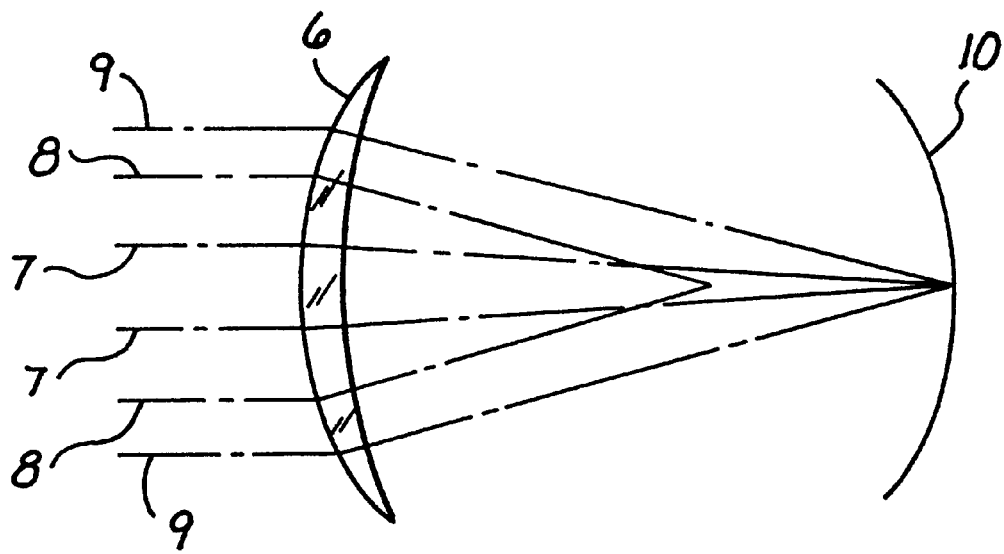
FIG. 1 is a schematic view illustrating the focusing of light of a prior art multifocal ophthalmic lens onto a retina.

These and other aspects of the present invention are apparent in the following detailed description and claims, particularly when considered in conjunction with the accompanying drawings in which like parts bear like reference numerals.

DETAILED DESCRIPTION OF THE PREFERRED EMBODIMENTS

Figure 2:
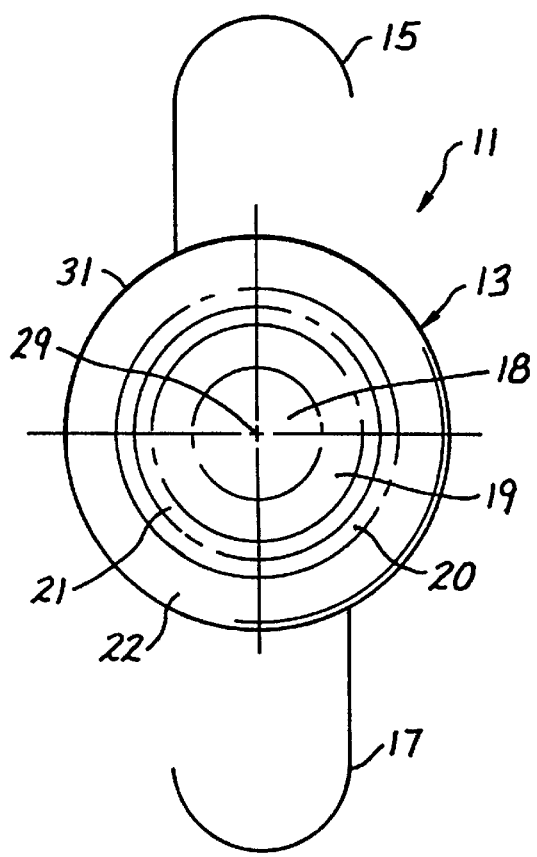
FIG. 2 is a plan view of an intraocular multifocal ophthalmic lens of the presently preferred embodiment.
Figure 3:
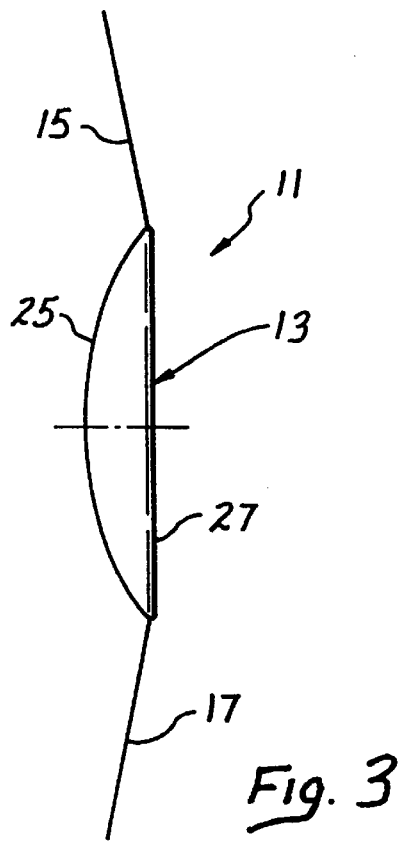
FIG. 3 is a side elevational view of the intraocular multifocal ophthalmic lens of the presently preferred embodiment.

FIGS. 2 and 3 show an intraocular lens 11, which comprises a circular optic 13 and two fixation members 15 and 17. The optic 13 may be constructed of rigid biocompatible materials, such as polymethylmethacrylate (PMMA), or flexible, deformable materials, such as silicone, hydrogel and the like which enable the optic to be rolled or folded for insertion through a small incision into the eye.

In the presently preferred embodiment, the fixation members 15 and 17 are fine hair-like strands or filaments which are attached to the optic 13 using conventional techniques. The fixation members 15 and 17 may be constructed of a suitable polymeric material, such as PMMA or polypropylene. Alternatively, the fixation members 15 and 17 may be integral with the optic 13. The optic 13 and the fixation members 15 and 17 may be of any desired number and configuration, and the configurations illustrated are purely illustrative.

The optic 13 has a central zone 18, inner and outer annular near zones 19 and 20, and annular far zones 21 and 22. In the presently preferred embodiment, the central zone 18 is circular, and the peripheries of the annular zones 19–22 are circular. The annular zones 19–22 circumscribe the central zone 18, and the zones are contiguous. The zones 19–22 are concentric and coaxial with the optic 13.

The zones 18–22 are used in describing the vision correction power of the optic 13, and they are arbitrarily defined. Thus, the peripheries of the zones 18–22 and the number of zones may be selected as desired. However to facilitate describing the optic 13, the peripheries of the annular zones 19–22 are considered to be the zero crossings in FIG. 4. Although the boundaries of the zones 18–22 are indicated by phantom lines in FIG. 2, it should be understood that the optic 13 has no such lines in any of its surfaces and that these lines constitute reference lines which define the zones.

As shown in FIG. 3, the optic 13 has a convex anterior surface 25 and a planar posterior surface 27; however, these configurations are merely illustrative. Although the vision correction power may be placed on either of the surfaces 25 and 27, in the presently preferred embodiment, the anterior surface 25 is appropriately shaped to provide the desired vision correction powers.

Figure 4:
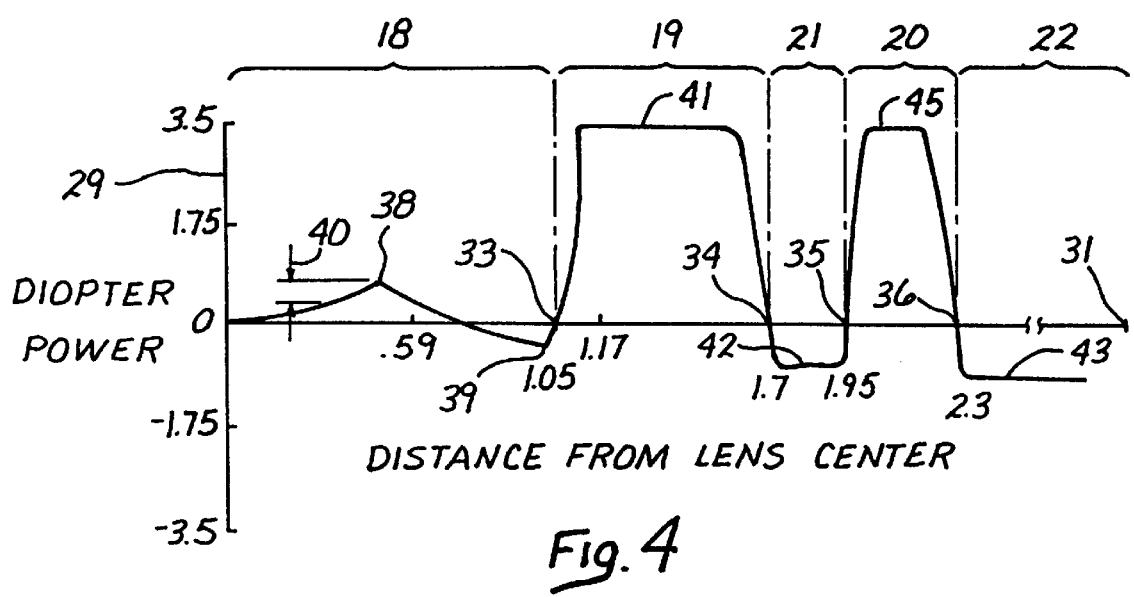
FIG. 4 is a plot of the power of the optic versus distance from the optic axis for the intraocular multifocal ophthalmic lens of the presently preferred embodiment.

FIG. 4 shows the preferred manner in which the vision correction power of the optic 13 varies from the center or optical axis 29 of the optic 13 to the circular outer periphery 31 of the optic. A preferred power distribution curve for a corneal inlay may be similar, or identical, to the curve of FIG. 4.

In FIG. 4, the vertical or "Y" axis represents the variation in diopter power of the optic 13 from the baseline or far vision correction power, and the "X" or horizontal axis shows the distance outwardly from the optical axis 29 in millimeters. Thus, the zero-diopter or baseline power of FIG. 4 is the power required for far vision for a conventional mono-focal intraocular lens. The power variation shown in FIG. 4 is applicable to any radial plane passing through the optical axis 29. In other words, the power at any given radial distance from the optical axis 29 is the same.

The central zone 18 extends from the optical axis 29 to a circular periphery 33, the first annular near zone 19 is considered as extending from the periphery 33 to a circular periphery 34, and the outer annular near zone 20 is considered as extending from a periphery 35 to a periphery 36. The negative diopter power of the two zones 21, 22 are of less power than required for far vision and may be considered as far, far vision correction powers. The annular far, far zone 21 extends between the peripheries 34 and 35, and the annular far, far zone 22 extends from the periphery 36 radially outwardly to the outer periphery 31 of the optic 13. As shown in FIG. 4, the vision correction power crosses the "X" axis or baseline at the peripheries 33, 34, 35 and 36.

As shown in FIG. 4, the vision correction power varies progressively and continuously from a baseline diopter power at the optical axis 29 to an apex 38 and then decreases continuously and progressively from the apex 38 back through the baseline diopter power to a negative diopter power at a point 39. From the point 39, the vision correction power increases continuously and progressively through the periphery 33 into the inner annular near zone 19. Of course, the diopters shown on the ordinate in FIG. 4 are merely exemplary, and the actual correction provided will vary with the prescription needs of the patient.

The apex 38 has a vision correction power for intermediate vision. The intermediate vision correction powers may be considered as being in a zone 40 which may be between 0.5 and 0.75 diopters from the baseline diopter power, as presently embodied. The far vision correction powers may be considered as lying between the zone 40 and the baseline diopter correction, and the far, far vision correction powers are negative. The intermediate, far, and far, far powers combine to provide a mean power in the central zone 18.

Within the inner annular near zone 19, the vision correction power varies continuously and progressively from the periphery 33 to a plateau 41; and from the plateau 41, the vision correction power varies continuously and progressively back to the periphery 34 at the baseline.

In the far, far zone 21 the vision correction power is below the far zone correction power, and is substantially constant. This vision correction power returns to the baseline at the periphery 35.

In the outer annular near zone 20, the power varies continuously and progressively from the periphery 35 to a plateau 45, and returns continuously and progressively from the plateau 45 to the baseline at the periphery 36.

In the far, far zone 22, the vision correction power is substantially constant, below the baseline vision correction power. The substantially constant vision correction power of the far, far zone 22 is slightly lower than the substantially constant vision correction power of the far, far zone 21, as presently embodied. The vision correction power of the far, far zone 22 remains negative from the periphery 36 to the baseline correction power at the outer periphery 31.

The inner near zone 19 has regions adjacent the peripheries 33 and 34 with far vision correction powers and a second region, which includes the plateau 41, with near vision correction powers. Similarly, the outer near zone 20 has regions adjacent the peripheries 35 and 36 with far vision correction powers and a second region, which includes the plateau 45, with near vision correction powers. For example, the near vision powers may be those which are above 2 or 2.5 diopters. The 2 to 2.5 diopters correspond to about 20 to 15 inches, respectively, of working distance, and this distance corresponds to the beginning of near activities. The two far, far vision correction plateaus 42, 43 of the two far, far annular zones 21, 22, respectively, preferably comprise diopter powers approximately one fifth of the distance between the baseline and the plateaus 41, 45, but located below the baseline.

As shown in FIG. 4, each of these "near" regions has a major segment, i.e., the plateaus 41 and 45 in which the near vision correction power is substantially constant. The plateau 41, which lies radially inwardly of the plateau 45, has a greater radial dimension than the plateau 45. The difference in radial dimension of the plateaus 41 and 45 allows these two plateaus to have approximately the same area.

Only a relatively small portion of the anterior surface 25 (FIG. 3) is dedicated to intermediate vision powers. This can be seen by the relatively small radial region which corresponds to the intermediate zone 40 (FIG. 4) and by the rapid change in diopter power between the plateaus 41 and 45 and the baseline diopter axis.

Figure 5:
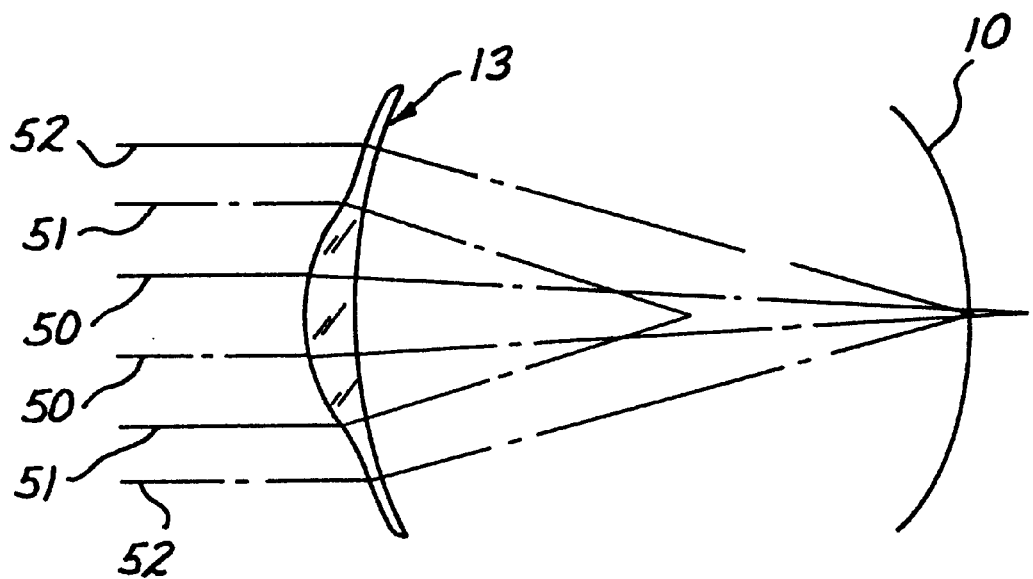
FIG. 5 is a schematic view illustrating the focusing of light of the intraocular multifocal ophthalmic lens of the presently preferred embodiment onto a retina.

The diagrammatic view of FIG. 5 shows how the multifocal ophthalmic lens 13 of the present invention focuses parallel light onto a retina 10 of the eye, in dim lighting conditions. The parallel rays 50 pass through the central portion 18 of the multifocal ophthalmic lens 13, and are focused onto the retina 10. The rays 51 pass through the intermediate focus region 40 of the central zone 18, and are focused in an area between the retina 10 and the multifocal ophthalmic lens 13. The rays 52 pass through the plateau 41 of the near zone 19 and, depending upon the lighting conditions, pass through the plateaus 42, 43 of the two far, far zones 21, 22, and the plateau 45 of the near zone 20. These rays 52 are focused slightly behind the retina 10. In the presently preferred embodiment, the distance at which the rays 52 are focused behind the retina 10, is approximately one-fifth of the distance at which the rays 51 are focused in front of the retina 10. The combination of the rays 50, 51, and 52 combine to form a best quality image on the retina 10 in dim lighting conditions.

While this invention has been described with respect to various specific examples and embodiments, it is to be understood that the invention is not limited thereto and that it can be variously practiced within the scope of the following claims.

What is claimed is:

1. A multifocal ophthalmic lens for providing vision correction powers, the multifocal ophthalmic lens being adapted to be implanted in an eye or to be disposed in a cornea and having a baseline diopter power for far vision correction, the multifocal ophthalmic lens comprising:

a central zone having a vision correction power approximately equal to or greater than the baseline diopter power;

a first outer zone located radially outwardly of the central zone and having a vision correction power greater than the baseline diopter power;

a second outer zone located radially outwardly of the first outer zone and having a substantially constant diopter power, which is less than the baseline diopter power, the multifocal ophthalmic lens having a mean vision correction power approximately equal to the baseline diopter power; and a third outer zone circumscribing the second outer zone and having a near vision correction power.

2. The multifocal ophthalmic lens according to claim 1, wherein the central zone has a progressive power region in which the vision correction powers vary progressively and in radially outwardly extending order from a far vision correction power, to an intermediate vision correction power, to a far vision correction power, and then to a diopter power which is less than the baseline diopter power.

3. The multifocal ophthalmic lens according to claim 2, wherein the first outer zone is contiguous with the central zone and has a far vision correction power adjacent the central zone and a region having a near vision correction power, the vision correction power of the first outer zone between the far and near vision correction powers being progressive.

4. The multifocal ophthalmic lens according to claim 3, wherein the first outer zone is annular and circumscribes the central zone.

5. A multifocal ophthalmic lens for providing vision correction powers, the multifocal ophthalmic lens being adapted to be implanted in an eye or to be disposed in a cornea and having a baseline diopter power for far vision correction, the multifocal ophthalmic lens comprising:

a central zone having a vision correction power approximately equal to or greater than the baseline diopter power, the central zone having a progressive power region in which the vision correction powers vary progressively and in radially outwardly extending order from a far vision correction power, to an intermediate vision correction power, to a far vision correction power, and then to a diopter power which is less than the baseline diopter power;

a first outer zone located radially outwardly of the central zone and having a vision correction power greater than the baseline diopter power, the first outer zone being contiguous with the central zone and has a far vision correction power adjacent the central zone and a region having a near vision correction power, the vision correction power of the first outer zone between the far and near vision correction powers being progressive;

a second outer zone located radially outwardly of the first outer zone and having a substantially constant diopter power, which is less than the baseline diopter power, the multifocal ophthalmic lens having a mean vision correction power approximately equal to the baseline diopter power; and a third outer zone circumscribing and being continuous with the second outer zone, the third outer zone having a far vision correction power adjacent the second outer zone and a region having a near vision correction power, the vision correction power of the third outer zone between the far and near vision correction powers being progressive.

6. The multifocal ophthalmic lens according to claim 5, further comprising a fourth outer zone circumscribing the third outer zone, and wherein the fourth outer zone has a substantially constant vision correction power, which is less than the baseline diopter power.

7. The multifocal ophthalmic lens according to claim 5, wherein the near vision correction power of the first outer zone is approximately equal in magnitude to the near vision correction power of the third outer zone.

* * * * *